(12) United States Patent  
Spiegler

(10) Patent No.: US 6,416,458 B1
(45) Date of Patent: Jul. 9, 2002

(54) THERAPEUTIC FLEXIBLE MAGNETIC SHEET AND METHOD

(75) Inventor: Bruce P. Spiegler, Smithtown, NY (US)

(73) Assignee: Therion Research Inc., Bay Shore, NY (US)

( * ) Notice: Subject to any disclaimer, the term of this patent is extended or adjusted under 35 U.S.C. 154(b) by 0 days.

(21) Appl. No.: 09/615,284

(22) Filed: Jul. 12, 2000

(51) Int. Cl.$^7$ .................................................. A61N 2/00
(52) U.S. Cl. ............................................................ 600/9
(58) Field of Search ....................................... 600/9–15

(56) References Cited

U.S. PATENT DOCUMENTS

| | | | |
|---|---|---|---|
| 3,764,539 A | 10/1973 | Cochardt et al. | 252/62.54 |
| 3,903,228 A | 9/1975 | Riedl et al. | 264/108 |
| 3,921,620 A | 11/1975 | Nakayama | 128/1.3 |
| 4,143,435 A | 3/1979 | Masuda | 5/345 R |
| 4,162,672 A | 7/1979 | Yazaki | 128/1.3 |
| 4,303,062 A | 12/1981 | Vars | 128/1.3 |
| D269,375 S | 6/1983 | Masuda | D24/36 |
| 4,391,270 A * | 7/1983 | Uragami | 600/15 |
| 4,480,596 A | 11/1984 | Shumiyashu | 128/1.3 |
| 4,489,711 A | 12/1984 | Latzke | 128/1.3 |
| 4,549,532 A * | 10/1985 | Baermann | 600/9 |
| 4,587,956 A * | 5/1986 | Griffin et al. | 600/15 |
| 4,798,194 A | 1/1989 | Amishima | 128/9 |
| 4,843,738 A * | 7/1989 | Masuda | 36/44 |
| 4,945,900 A | 8/1990 | Masuda | 128/57 |
| 4,983,851 A | 1/1991 | Masuda et al. | 250/493.1 |
| 5,035,017 A * | 7/1991 | Komuro | 600/9 X |
| 5,123,406 A | 6/1992 | Masuda | 128/57 |
| 5,138,730 A | 8/1992 | Masuda | 5/481 |
| 5,172,436 A | 12/1992 | Masuda | 5/448 |
| 5,295,494 A | 3/1994 | Rodriguez | 128/845 |
| 5,304,111 A * | 4/1994 | Mitsuno et al. | 600/9 |
| 5,312,321 A | 5/1994 | Holcomb | 600/9 |
| 5,575,760 A | 11/1996 | Masuda | 601/19 |
| 5,621,369 A | 4/1997 | Gardner et al. | 335/302 |
| 5,700,234 A | 12/1997 | Masuda | 600/15 |
| 5,782,743 A | 7/1998 | Russell | 600/9 |
| D398,965 S | 9/1998 | Masuda | D23/259 |
| 5,803,896 A | 9/1998 | Chen | 600/9 |
| 5,817,000 A | 10/1998 | Souder | 600/15 |
| D402,011 S | 12/1998 | Masuda | D23/259 |
| 5,871,438 A * | 2/1999 | Ardizzone | 600/9 |
| 5,965,282 A | 10/1999 | Baermann | 428/692 |
| 5,984,856 A * | 11/1999 | Love | 600/15 |
| 6,126,589 A * | 10/2000 | Brooks | 600/15 |
| 6,267,720 B1 * | 1/2001 | Knox et al. | 600/15 |
| 6,267,719 B1 * | 7/2001 | Grisoni et al. | 600/15 |

OTHER PUBLICATIONS

"All Magnets Are Not Created Equal", Advertising Material, 1 page, no date.

"Advanced Magnetic Technology", Nikken, Advertising Materials, 19 pages, original brochure, 1999.

* cited by examiner

Primary Examiner—John P. Lacyk
Assistant Examiner—Joseph A Cadugan
(74) Attorney, Agent, or Firm—Kenyon & Kenyon

(57) ABSTRACT

A therapeutic device is disclosed. In an embodiment of the present invention, the therapeutic device includes a sheet having a plurality of magnetized areas defined by a grid. The grid includes a plurality of straight lines and a plurality of curved lines where the plurality of straight lines intersect the plurality of curved lines.

13 Claims, 2 Drawing Sheets

THERAPEUTIC FLEXIBLE MAGNETIC SHEET AND METHOD

BACKGROUND OF THE INVENTION

1. Field of the Invention

The present invention relates to magnets and more particularly to therapeutic flexible magnetic sheets.

2. Description of Related Art

Flexible magnetic sheets have been disclosed for various uses. One of the primary uses of such devices is for therapeutic use on humans such as for suppressing nerve cell action and increasing blood flow to reduce pain. There are numerous devices that have attempted to maximize the effect of such therapeutic use of magnets.

There are several design factors that determine the degree of effectiveness of a multi-polar therapeutic magnetic device. A consideration in the design of such devices is known as the Hall effect. It is desirable that a multi-polar magnetic field intersect the blood vessels at as close to an angle of ninety degrees as possible. The magnitude of the therapeutic effect may decrease proportionally with the degree of deviation from ninety degrees. For example, a magnetic field running parallel to a blood vessel may have no therapeutic effect.

Examples of approaches that attempt to achieve a maximum therapeutic effect are as follows. Magnetic belts are known that have a pattern of discrete permanent magnet discs received in circular holes arranged in a rectangular pattern in a substrate, such as a flexible magnetic material, for imparting a magnetic flux normal to the material in the lumbar region to reduce stiffness or pain.

Other approaches include a magnetic plaster formed of an elastic magnetizable plastic sheet material, magnetized in a series of parallel stripes of alternating polarity, at a spacing of 4–10 mm. This arrangement is a basic parallel line multi-polar pattern that is designed to enable positioning of the sheet on the patient's skin with the stripes oriented transversely to the patient's vasculature so that blood flow traverses the alternating poles. However, there are several possible orientations in which the vasculature will be unaffected by the magnetic field.

It is also known to use a magnetic sheet which arranges the magnetic poles in a pattern which is concentric, angular or radial about a common axis or center. These arrangements are intended to permit the patient to position the sheet in any orientation on the skin and still have the pattern traverse the underlying vasculature. However, these arrangements have several limitations.

The patterns of such arrangements cannot be expanded indefinitely in size to cover large areas of a patient's body. As the pattern is scaled to larger sizes, the circumferential extent of each area of one polarity increases to the point where it is no longer effective to induce any changes in magnetic flux. For example, in the concentric case, each ring becomes very large at a distance spaced from the center; so large that an underlying blood vessel oriented tangentially to the pattern can travel a substantial distance without crossing a magnetic polarity boundary. The same situation can result in the angular or radial pattern. Additionally, as the angular or radial pattern is enlarged, the lengths of segments increase so that a blood vessel, aligned lengthwise to the segment, does not necessarily cross areas of alternating polarity. Moreover, if the blood vessel does not traverse the apparatus directly through the center, there is no possibility of achieving a ninety degree intersection with a polarity boundary line.

Other approaches attempt to improve upon the arrangements discussed above by providing curved first and second areas of alternating magnetic polarity. However, there is still a possibility that a blood vessel could have no intersection when it is oriented at a forty-five degree angle that does not pass through a north pole circle of the magnet.

Accordingly, there is a need in the art for an improved therapeutic flexible magnetic sheet.

SUMMARY OF THE INVENTION

A therapeutic device is provided. In an embodiment of the present invention, the therapeutic device includes a sheet having a plurality of magnetized areas defined by a grid. The grid includes a plurality of straight lines and a plurality of curved lines where the plurality of straight lines intersect the plurality of curved lines.

DETAILED DESCRIPTION

Figure 1:
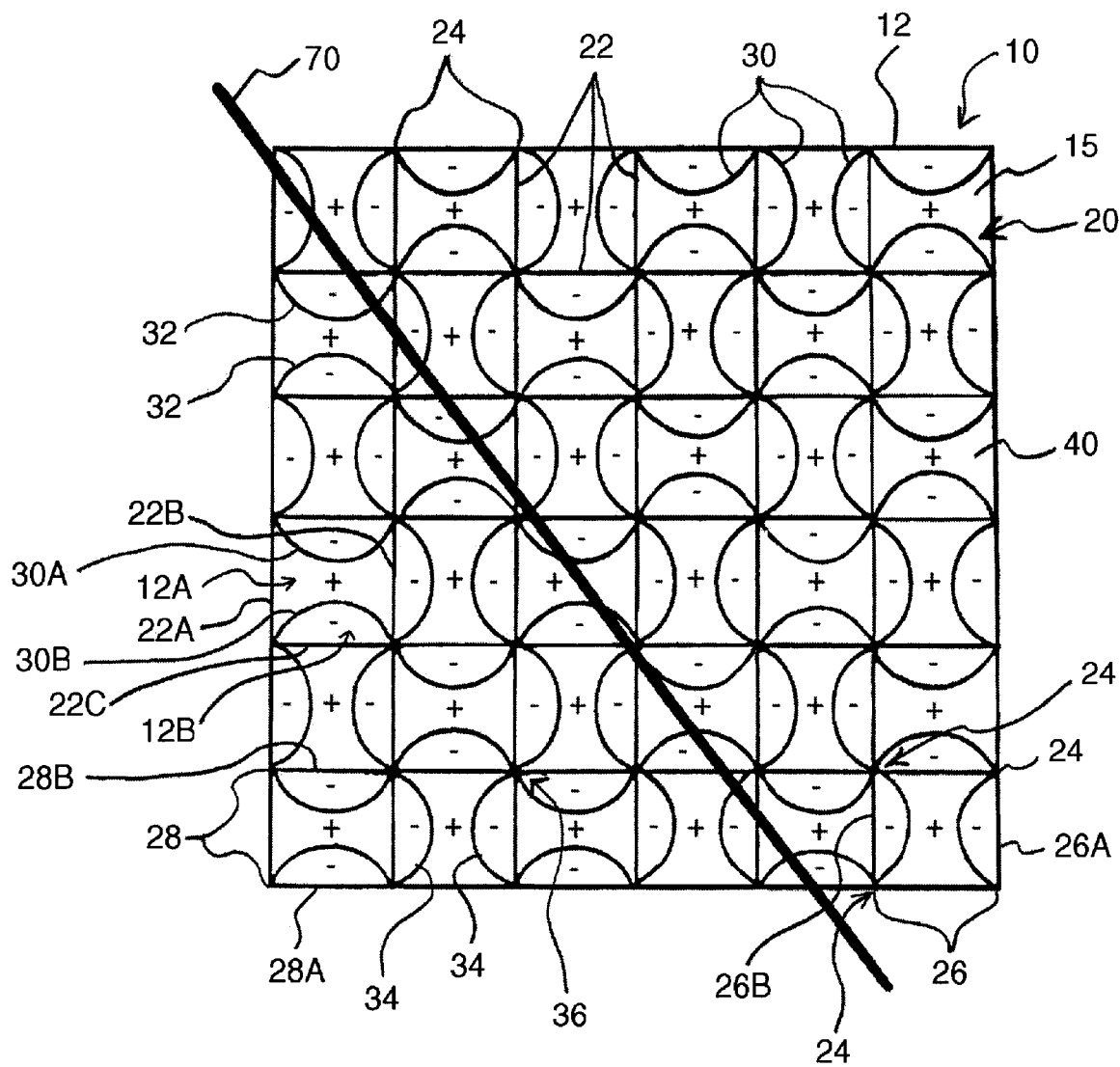
FIG. 1 is a plan view of an embodiment of a therapeutic device in accordance with the present invention.

As can be seen in FIG. 1, the therapeutic device of the present invention includes a flexible magnetic sheet 10. The flexible magnetic sheet 10 is a flexible sheet 12 that has a surface 15. The sheet 12 has a plurality of magnetized areas, e.g., areas 12A and 12B, which are defined by a grid 20 that includes straight lines 22 and curved lines 30. Straight lines 22 and curved lines 30 are lines of flux and define the boundaries of the magnetized areas. For example, straight line segments 22A, 22B and curved line segments 30A, 30B define magnetized area 12A of positive polarity. Similarly, straight line segment 22C and curved line segment 30B define magnetized area 12B of negative polarity.

Adjacent magnetized areas, i.e., those areas that share a common boundary line, have opposed polarities. Thus, a multi-polar magnetic sheet is provided. For example, magnetized area 12A, which shares boundary line 30B with adjacent magnetized area 12B, has a positive polarity and area 12B has a negative polarity. Each magnetized area is defined by at least one straight line 22 and one curved line 30.

The magnetized areas may be formed by permanent magnetic material embedded in the sheet. The process of embedding magnetic material is known by those skilled in the art. Magnets may alternatively be applied to the outer surface of the flexible magnetic sheet.

As discussed above, grid 20 is defined by a plurality of straight lines 22 and a plurality of curved lines 30. The vertical straight lines 22 in the grid 20 are parallel to each other and the horizontal straight lines 22 in the grid 20 are parallel to each other. The vertical straight lines 22 are perpendicular to the horizontal straight lines 22. As such, the vertical straight lines 22 intersect perpendicularly with the horizontal straight lines 22 at intersection points 24. The straight lines 22 are not required to be precisely straight nor precisely perpendicular to other of the straight lines. Rather, the lines 22 are only required to be substantially straight and substantially perpendicular such that the magnetic field of the present invention can be achieved.

As a further description of the orientation of the straight lines as discussed above, as can be seen in FIG. 1, the grid includes a first set of straight lines 26 where a first straight line 26A in the first set of straight lines is oriented parallel to a second straight line 26B in the first set of straight lines. The grid also includes a second set of straight lines 28 where a first straight line 28A in the second set of straight lines is oriented parallel to a second straight line 28B in the second set of straight lines. The first set of straight lines 26 is oriented perpendicular to the second set of straight lines 28 such that they intersect at intersection points 24.

The curved lines 30 may extend vertically and/or horizontally through the grid 20. For example, FIG. 1 illustrates a first plurality of curved lines 32 that extend horizontally through the grid 20 and a second plurality of curved lines 34 that extend vertically through the grid 20. The curved lines 30 on the magnetic sheet of the present invention may be sinusoidal in configuration. As such, half of one period of the sine curve 30 may reside between adjacent vertical lines 22 and between adjacent horizontal lines 22. The zero value point 36 of the sine curves 30 may intersect with the intersection points 24. Adjacent sine curves 30 which extend in the same direction, i.e., either horizontal or vertical, may be shifted 180 degrees out of phase from each other.

In the embodiment of FIG. 1, as discussed above, the straight lines intersect at right angles and the curved lines intersect the straight lines at their intersection points. Each of the plurality of curved lines intersect at least one of the plurality of straight lines at at least one of the intersection points.

Figure 2:
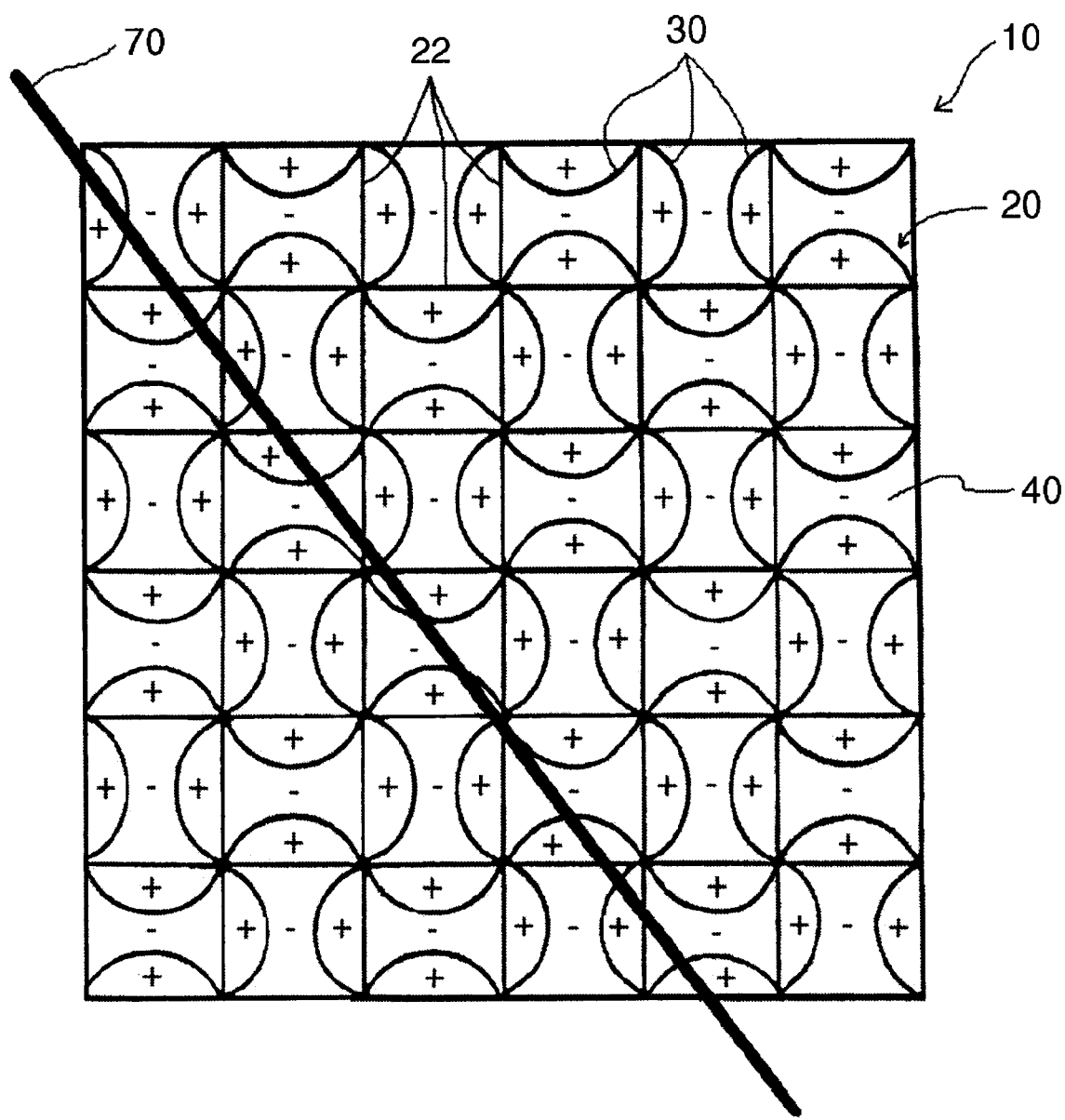
FIG. 2 is a plan view of an alternative embodiment of a therapeutic device in accordance with the present invention.

Whereas FIG. 1 illustrates a particular alternating polarity pattern, the present invention is not limited to the particular alternating polarity pattern illustrated and other alternating polarity patterns are contemplated in the present invention. For example, FIG. 2 illustrates another embodiment for an alternating polarity pattern. As can be seen, the embodiment of FIG. 2 still utilizes a grid 20 of intersecting straight lines 22 and curved lines 30, as described above. However, in contrasting the polarity pattern of FIG. 1 with that of FIG. 2, magnetic area 40 in the embodiment of FIG. 1 has a positive polarity and magnetic area 40 in the embodiment of FIG. 2, which is the same geographic area as that in FIG. 1, has a negative polarity.

Additionally, the present invention may utilize other patterns of alternating polarity areas which are defined by intersecting straight and curved lines and the present invention is not limited to having any particular pattern or to having any particular polarity at any particular area on the magnetic sheet. Thus, the alternating polarity patterns may vary in their configuration.

As can be seen in FIGS. 1 and 2, a blood vessel 70 that traverses the flexible magnetic sheet 10 in virtually any direction will cross numerous magnetic areas at, or close to, a ninety degree angle with respect to a boundary line of the magnetic area. FIGS. 1 and 2 illustrate proposed paths for a blood vessel 70 across the magnetic areas and, as can be seen, the blood vessel bisects numerous boundary lines at, or close to, a ninety degree angle, providing an enhanced therapeutic effect.

In another aspect of the invention, a method of achieving a therapeutic effect is provided. In order to achieve a therapeutic effect on a patient, a flexible magnetic sheet 12 having a plurality of magnetized areas defined by a grid, which may be accomplished by a permanent magnetic material embedded therein, is provided. As described above, the grid includes intersecting curved and straight lines. Adjacent magnetic areas have opposed polarities. The flexible magnetic sheet 12 is oriented on the patient's body such that the underlying vascular structure 70 of the body crosses at least one of the boundary lines which define the magnetic areas at, or close to, a ninety degree angle. As discussed above, and as illustrated in FIGS. 1 and 2, the present invention will allow numerous crossings of the vascular structure at, or close to, a ninety degree angle to the boundaries of the magnetic areas.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the claims and their equivalents.

What is claimed is:

1. A therapeutic device, comprising:
   a sheet having a plurality of magnetized areas of alternating polarity defined by a grid, said grid including:
      a plurality of straight lines including:
         a first set of straight lines wherein a first straight line in said first set of straight lines is oriented parallel to a second straight line in said first set of straight lines; and
         a second set of straight lines wherein a first straight line in said second set of straight lines is oriented parallel to a second straight line in said second set of straight lines;
      a plurality of curved lines;
      wherein said first set of straight lines is oriented perpendicular to said second set of straight lines such that they intersect at intersection points and wherein each of said plurality of curved lines intersect at least one of said plurality of straight lines at at least one of said intersection points so that each of said intersection points is intersected by at least one of said plurality of curved lines.

2. The therapeutic device of claim 1, wherein each magnetized area of said plurality of magnetized areas is defined by at least one of said plurality of straight lines and at least one of said plurality of curved lines.

3. The therapeutic device of claim 1, wherein said plurality of curved lines are horizontal.

4. The therapeutic device of claim 1, wherein said plurality of curved lines are vertical.

5. The therapeutic device of claim 1, wherein a first plurality of said plurality of curved lines are horizontal and a second plurality of said plurality of curved lines are vertical.

6. The therapeutic device of claim 1, wherein said plurality of curved lines are sinusoidal curves.

7. The therapeutic device of claim 6, wherein adjacent sinusoidal curves are 180 degrees out of phase.

8. The therapeutic device of claim 6, wherein the first set of straight lines and the second set of straight lines form squares, the squares having a height, the sinusoidal curves having a maximum height of less than half the height of the squares.

9. A therapeutic device, comprising:
   a flexible sheet of material having a plurality of magnetized areas of alternating polarity defined by a grid;
   said grid including intersecting curved lines and straight lines;
   wherein said straight lines include:
      a first set of straight lines wherein a first straight line in said first set of straight lines is oriented parallel to a second straight line in said first set of straight lines; and a second set of straight lines wherein a first straight line in said second set of straight lines is oriented parallel to a second straight line in said second set of straight lines; and wherein said first set of straight lines is oriented perpendicular to said second set of straight lines such that they intersect at intersection points; and wherein said curved lines are sinusoidal and wherein each of said curved lines intersect at least one of said straight lines at at least one of said intersection points, so that each of said intersection points is intersected by at least one of said plurality of curved lines.

10. The therapeutic device of claim 9, wherein adjacent sinusoidal curves are 180 degrees out of phase.

11. The therapeutic divice of claim 9, wherein a first of said sinusoidal curves is oriented horizontally and a second of said sinusoidal curves is oriented vertically.

12. The therapeutic device of claim 9, wherein the first set of straight lines and the second set of straight lines form squares, the squares having a height, the sinusoidal curves having a maximum height of less than half the height of the squares.

13. A method of providing a therapeutic effect, comprising:

providing a flexible magnetic sheet having a plurality of magnetized areas of alternating polarity defined by a grid, said grid including intersecting curved lines and straight lines;

wherein said straight lines include:
    a first set of straight lines wherein a first straight line in said first set of straight lines is oriented parallel to a second straight line in said first set of straight lines; and
    a second set of straight lines wherein a first straight line in said second set of straight lines is oriented parallel to a second straight line in said second set of straight lines; and wherein said first set of straight lines is oriented perpendicular to said second set of straight lines such that they intersect at intersection points; and wherein said curved lines are sinusoidal and wherein each of said curved lines intersect at least one of said straight lines at at least one of said intersection points, so that each of said intersection points is intersected by at least one of said plurality of curved lines; and orienting said flexible magnetic sheet on a body such that an underlying vascular structure of the body crosses at least one of said curved and straight lines at, or close to, a 90 degree angle.

\* \* \* \* \*